United States Patent [19]
Manley

[11] Patent Number: 5,905,156
[45] Date of Patent: May 18, 1999

[54] BENZOPYRANS AND PHARMACEUTICAL COMPOSITIONS CONTAINING THEM

[75] Inventor: Paul W. Manley, Arlesheim, Switzerland

[73] Assignee: Novartis AG, Basel, Switzerland

[21] Appl. No.: 08/952,549

[22] PCT Filed: May 24, 1996

[86] PCT No.: PCT/EP96/02257

§ 371 Date: Nov. 20, 1997

§ 102(e) Date: Nov. 20, 1997

[87] PCT Pub. No.: WO97/37490

PCT Pub. Date: Nov. 28, 1996

[30] Foreign Application Priority Data

May 24, 1995 [GB] United Kingdom .................. 9510477

[51] Int. Cl.[6] ...................... C07D 401/00; C07D 401/04; A61K 31/445; A61K 31/35
[52] U.S. Cl. ........................ 546/196; 546/282.7; 546/153; 514/320; 514/337; 514/312; 514/456; 549/404
[58] Field of Search ........................... 546/196, 17, 282.7, 546/153; 548/525; 514/422, 320, 278, 456, 337, 312; 549/404

[56] References Cited

U.S. PATENT DOCUMENTS

| | | | |
|---|---|---|---|
| 5,236,935 | 8/1993 | Yoo et al. | 514/337 |
| 5,300,511 | 4/1994 | Yoo et al. | 514/278 |
| 5,310,753 | 5/1994 | Englert et al. | 514/422 |

FOREIGN PATENT DOCUMENTS

| | | |
|---|---|---|
| 0 488 301 A1 | 6/1992 | European Pat. Off. . |
| 0 514 942 A1 | 11/1992 | European Pat. Off. . |
| 0 547 523 A1 | 6/1993 | European Pat. Off. . |

*Primary Examiner*—Deborah C. Lambkin
*Attorney, Agent, or Firm*—Carol A. Loeschorn

[57] ABSTRACT

The invention provides novel 2,2-di($C_{1-5}$alkyl)- or trans-2,2-di($C_{1-5}$alkyl)-3,4-dihydro-3-hydroxy- -4-carboxamido-6-(N-arylsulfonamido)-2H-1-benzopyrans; and N-oxides, esters and salts thereof; processes for their production; and their uses as pharmaceuticals, e.g. as $K^+$-channel openers, bronchodilators and agents for the suppression of airways hyperreactivity, e.g., for use in the treatment of asthma.

19 Claims, No Drawings

BENZOPYRANS AND PHARMACEUTICAL COMPOSITIONS CONTAINING THEM

This application is a 371 of PCT/EP96/02257 filed May 24, 1996.

The present invention relates to novel 2,2-dialkyl- and 2,2-dialkyl-3,4-dihydro-3-hydroxy-2H-1-benzopyrans, and salts, esters and N-oxides thereof, and to processes for their production, as well as to their use as pharmaceuticals and pharmaceutical compositions comprising them.

More particularly the present invention provides in its broadest aspect:

1) A 2,2-di($C_{1-5}$alkyl)- or trans-2,2-di($C_{1-5}$alkyl)-3,4-dihydro-3-hydroxy-4-carboxamido-6-(N-arylsulfonamido)-2H-1-benzopyran; or an N-oxide thereof; or a physiologically-hydrolysable and -acceptable ester of such a benzopyran or N-oxide; or acid addition or quarternary ammonium salt of such a benzopyran, N-oxide or ester.

Alkyl groups and moieties of compounds as defined under 1) above may be branched or straight chain. Suitable arylsulfonamido moieties include sulfonamido which is N-substituted with aryl, or N,N-di-substituted with aryl and $C_{1-5}$alkyl, or N,N-disubstituted with aryl and $C_{2-5}$alkylene linked to the aryl to form a bicyclic structure, e.g., a tetrahydroquinolinyl moiety. The term "aryl" includes mono- or bicyclic aromatic groups optionally containing one or more nitrogen atoms, e.g., phenyl, napthyl or pyridyl, which may be optionally substituted, e.g., with up to three substituents, e.g., selected from halogen, $C_{1-5}$alkyl, (halo)$_{1-3}$-$C_{1-5}$alkyl, or $C_{1-5}$alkoxy, especially phenyl, fluorophenyl, trifluoromethylphenyl, methoxyphenyl, or pyridyl.

As hereinafter described, compounds of the present invention, e.g. as defined under 1 above, have potassium ($K^+$) channel opening activity [see e.g. Cook et al., "Potassium Channels: Structure, Classification, Function and Therapeutic Potential", ed. N. S. Cook, Ellis Horwood, Chichester (1990), p.p. 181–255]. Benzopyran derivatives which are carboxamido-substituted at the 4-position, having $K^+$-channel opening activity are extensively described in the art and comprise a substantial and recognisable compound class. The 4-carboxamido moiety in the compounds of the invention may comprise any of those known and described in the art in relation to $K^+$-channel opening benzopyrans including N-substituted, for example cyclic, carboxamido moieties. Preferred carboxamido moieties in relation to the compounds of the invention are those of the formula —N($R_9$)—$COR_{10}$ as defined below.

As will be appreciated, the benzopyran nucleus of compounds defined under 1 may bear substituents in addition to those specifically defined. In particular they may, for example, be 7-$C_{1-5}$alkyl substituted, especially 7-methyl substituted, e.g. as hereinafter indicated in relation to formula I.

In accordance with the present invention 2,2-di($C_{1-5}$alkyl)-3,4-dihydro-3-hydroxy-4-carboxamido-6-(N-arylsulfonamido)-2H-1-benzopyrans and/or -oxides, esters, and salts thereof as defined under 1 above are preferred. The 3-hydroxy group and the 4-carboxamido moiety in such compounds are disposed in the trans-configuration as specified under 1. For this compound group (3S,4R)-enantiomers will generally be preferred, whether in pure or substantially pure form or in isomeric, e.g. racemic, mixture as hereinafter described in relation to compounds of formula I.

In a more specific aspect the present invention provides:

2) A compound of formula I

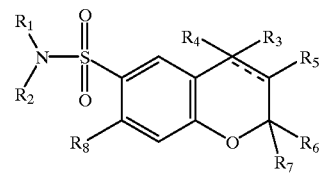

Formula I wherein $R_1$ is aryl, $R_2$ is H or $C_{1-5}$alkyl, or is $C_{2-5}$alkylene linked to $R_1$, $R_3$ is a group of formula —N($R_9$)—$COR_{10}$ wherein $R_9$ is hydrogen and $R_{10}$ is phenyl or pyridyl, or $R_9$ and $R_{10}$ together are 1,3-butadienylene or represent a group of formula —$(CH_2)_n$— or

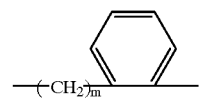

in which n is an integer of from 3 to 5 inclusive and m is 1 or 2, $R_4$ is hydrogen and $R_5$ is hydroxy in the trans position with respect to $R_3$, or $R_4$ and $R_5$ together represent an additional bond as indicated by the dotted line, $R_6$ and $R_7$ are, independently, $C_{1-5}$alkyl, and $R_8$ is hydrogen or $C_{1-5}$alkyl;

or N-oxide thereof, or physiologically-hydrolysable and -acceptable ester of such a compound or N-oxide, or acid addition or quarternary ammonium salt of such a compound, N-oxide or ester.

Alkyl groups as $R_2$, $R_6$, $R_7$ and $R_8$ may be branched or straight chain. $R_6$ and $R_7$ are both preferably methyl. $R_8$ is preferably hydrogen or methyl, most preferably hydrogen.

In a preferred group of compounds of formula I, $R_1$ is phenyl, fluorophenyl, trifluoromethylphenyl, methoxyphenyl, or pyridyl; and/or $R_2$ is methyl, ethyl, or H; or $R_1$ and $R_2$ together with N form a 1,2,3,4-tetrahydroquinolin-1-yl group.

In a further preferred group of compounds of formula I, in the definition of $R_3$, $R_9$ is hydrogen and $R_{10}$ is pyridyl (especially 3-pyridyl) or $R_9$ and $R_{10}$ together are 1,3-butadienylene, trimethylene or tetramethylene. Most preferably $R_9$ and $R_{10}$ together are tetramethylene.

Preferably $R_4$ is hydrogen and $R_5$ is hydroxy.

Especially preferred are compounds of formula Ia, Ib and Ic

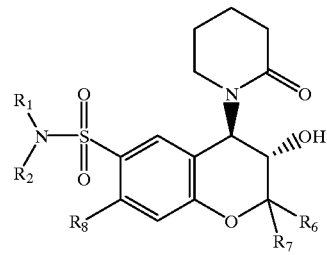

Formula Ia

-continued

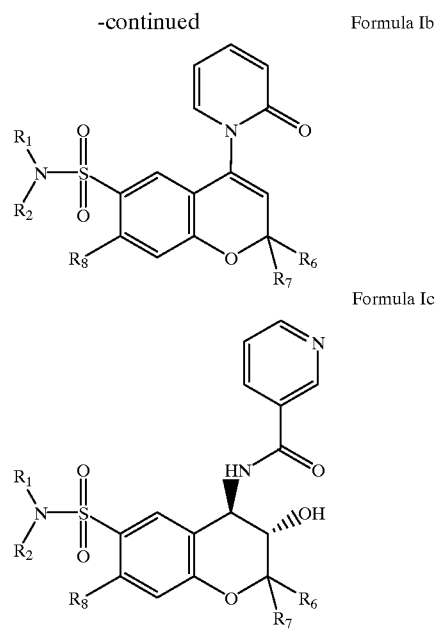

Formula Ib

Formula Ic wherein $R_1$, $R_2$, $R_6$, $R_7$, and $R_8$ are as defined above.

The 2,2-di($C_{1-5}$alkyl)- or trans-2,2-di($C_{1-5}$alkyl)-3,4-dihydro-3-hydroxy- -4-carboxamido-6-(N-arylsulfonamido)-2H-1-benzopyrans include the following compounds a. trans-1,2,3,4-tetrahydro-1-[[3,4-dihydro-2,2-dimethyl-3-hydroxy-4-(2-oxo-piperidin-1-yl)-2H-1-benzopyran-6-yl]sulphonyl]quinoline
b. trans-N-phenyl-3,4-dihydro-2,2-dimethyl-3-hydroxy-4-(2-oxo-piperidin-1-yl)-2H-1-benzopyran-6-sulphonamide
c. trans-N-(4-methoxyphenyl)-3,4-dihydro-2,2-dimethyl-3-hydroxy-4-(2-oxo-piperidin-1-yl)-2H-1-benzopyran-6-sulphonamide
d. trans-N-methyl-N-phenyl-3,4-dihydro-2,2-dimethyl-3-hydroxy-4-(2-oxo-piperidin-1-yl)-2H-1-benzopyran-6-sulphonamide
e. trans-N-methyl-N-(4-methoxyphenyl)-3,4-dihydro-2,2-dimethyl-3-hydroxy-4-(2-oxo-piperidin-1-yl)-2H-1-benzopyran-6-sulphonamide
f. trans-N-methyl-N-(3-methoxyphenyl)-3,4-dihydro-2,2-dimethyl-3-hydroxy-4-(2-oxo-piperidin-1-yl)-2H-1-benzopyran-6-sulphonamide
g. trans-N-methyl-N-(4-fluorophenyl)-3,4-dihydro-2,2-dimethyl-3-hydroxy-4-(2-oxo-piperidin-1-yl)-2H-1-benzopyran-6-sulphonamide
h. trans-N-methyl-N-(4-trifluoromethylphenyl)-3,4-dihydro-2,2-dimethyl-3-hydroxy-4 -(2-oxo-piperidin-1-yl)-2H-1-benzopyran-6-sulphonamide
i. trans-N-methyl-N-(3-trifluoromethylphenyl)-3,4-dihydro-2,2-dimethyl-3-hydroxy-4-(2-oxo-piperidin-1-yl)-2H-1-benzopyran-6-sulphonamide
j. trans-N-methyl-N-(pyridin-4-yl)-3,4-dihydro-2,2-dimethyl-3-hydroxy-4-(2-oxo-piperidin-1-yl)-2H-1-benzopyran-6-sulphonamide
k. trans-N-methyl-N-(pyridin-3-yl)-3,4-dihydro-2,2-dimethyl-3-hydroxy-4-(2-oxo-piperidin-1-yl)-2H-1-benzopyran-6-sulphonamide
l. trans-N-ethyl-N-phenyl-3,4-dihydro-2,2-dimethyl-3-hydroxy-4-(2-oxo-piperidin-1-yl)-2H-1-benzopyran-6-sulphonamide
m. trans-[3,4-dihydro-2,2-dimethyl-3-hydroxy-6-[(1,2,3,4-tetrahydroquinolin-1-yl)sulphonyl]-2H-1-benzopyran-4-yl]-3-pyridinecarboxamide
n. trans-[3,4-dihydro-2,2-dimethyl-3-hydroxy-6-[(N-methyl-N-phenylamino)sulphonyl]-2H-1-benzopyran-4-yl]-3-pyridinecarboxamide
o. trans-[3,4-dihydro-2,2-dimethyl-6-[(N-ethyl-N-phenylamino)sulphonyl]-3-hydroxy-2H-1-benzopyran-4-yl]-3-pyridinecarboxamide
p. trans-N-methyl-N-phenyl-3,4-dihydro-4-(1,2-dihydro-2-oxo-1-pyridyl)-2,2-dimethyl-3-hydroxy-2H-1-benzopyran-6-sulphonamide
q. N-methyl-N-phenyl-4-(1,2-dihydro-2-oxo-1-pyridyl)-2,2-dimethyl-2H-1-benzopyran-6-sulphonamide
r. (3S, trans)-N-methyl-N-phenyl-3,4-dihydro-4-(1,2-dihydro-2-oxo-1-pyridyl)-2,2-dimethyl-3-hydroxy-2H-1-benzopyran-6-sulphonamide
s. (3S, trans)-[3,4-dihydro-2,2-dimethyl-3-hydroxy-6-[(N-methyl-N-phenylamino)sulphonyl]-2H-1-benzopyran-4-yl]-3-pyridinecarboxamide
t. (3S, trans)-[3,4-dihydro-2,2-dimethyl-3-hydroxy-6-[(1,2,3,4-tetrahydroquinolin-1-yl)sulphonyl]-2H-1-benzopyran-4-yl]-3-pyridinecarboxamide
u. (3S, trans)-N-phenyl-3,4-dihydro-2,2-dimethyl-3-hydroxy-4-(2-oxo-piperidin-1-yl)-2H-1-benzopyran-6-sulphonamide Especially preferred compounds of formula I are the compounds of formula Ia, Ib, or Ic wherein $R_1$ is phenyl;

$R_2$ is H or methyl, or is trimethylene linked to $R_1$ so that $R_1$ and $R_2$ together with N form a 1,2,3,4-tetrahydroquinolin-1-yl group;

$R_6$ and $R_7$ are both methyl; and $R_8$ is hydrogen.

Certain benzopyrans of the invention form N-oxides, e.g. at the nitrogen atom of a pyridyl group. Such N-oxides have comparable activity (as hereinafter described) and tolerability to the parent compounds and also form part of the present invention.

By "physiologically-hydrolysable and -acceptable ester" as used herein is meant an ester in which a hydroxy group (e.g., in relation to formula I, the hydroxy group $R_5$) is esterified and which is hydrolysable under physiological conditions to yield an acid which is itself physiologically tolerable at doses to be administered. As will be appreciated such esters are pro-drug forms of conventional type and have comparable activity and tolerability to the parent compounds. Examples of such esters include esters of $C_{2-5}$ carboxylic acid, benzoic acid, and salicylic acid.

Acid addition salts, e.g. of compounds of formula I, their N-oxides and defined esters thereof, include salts with both inorganic and organic acids. Such salts also have comparable activity to the free compounds, N-oxides and esters. Pharmaceutically acceptable acid addition salts for pharmaceutical use in accordance with the present invention as hereinafter described include e.g. hydrochloric, sulphuric and fumaric acid salts.

Quarternary ammonium salts, e.g. of compounds of formula I, their N-oxides and defined esters thereof, include e.g. salts with organo-halides, e.g. alkyl halides. Pharmaceutically acceptable quarternary ammonium salts for pharmaceutical use in accordance with the present invention include e.g. such salts with methyl iodide.

For pharmaceutical use in accordance with the present invention ester forms as aforesaid are generally less preferred.

Compounds of formula I in which $R_4$ is hydrogen and $R_5$ is hydroxy, as well as their N-oxides, esters and salts as aforesaid, have the configuration (3S*,4R*), i.e. the configuration of the groups $R_3$ and $R_5$ at the 3- and 4-positions is trans. Compounds of the invention thus exist in enantiomeric form, i.e. as optically active antipodes having the [3S,4R] or [3R,4S] configuration. The present invention is to be understood as embracing both the individual enantiomers (optically active, [3S,4R] or [3R,4S], antipodes) as well as mixtures, e.g. racemic mixtures, thereof.

In that pharmaceutical utility in accordance with the invention is believed to reside, or reside predominantly, in the [3S,4R] enantiomers, these are preferred. Suitably the said [3S,4R] enantiomers will be, or will be employed in accordance with the invention, in purified form, i.e. comprising less than 50% enantiomeric contaminants, more suitably in pure or substantially pure form, e.g. comprising less than 10%, preferably 5% or less, e.g. 1 or 2% or less of [3R,4S] enantiomeric contaminants.

Compounds according to 1) or 2) above, e.g., of formula I may be prepared from the corresponding 1a,7b-dihydro-2,2-di($C_{1-5}$alkyl)-6-(aryl (or 2,2-dimethylpropyl) sulfonamido)-2H-oxireno[c][1]benzopyran (e.g., Intermediate 2 below), as more fully described below, in accordance with the following Reaction Scheme A (wherein Hal is halogen, preferably bromine, M is a metal or metal halide, e.g., lithium or magnesium halide (Hal-Mg-, e.g., BrMg-), and the R groups are as defined for formula I above):

Reaction Scheme A

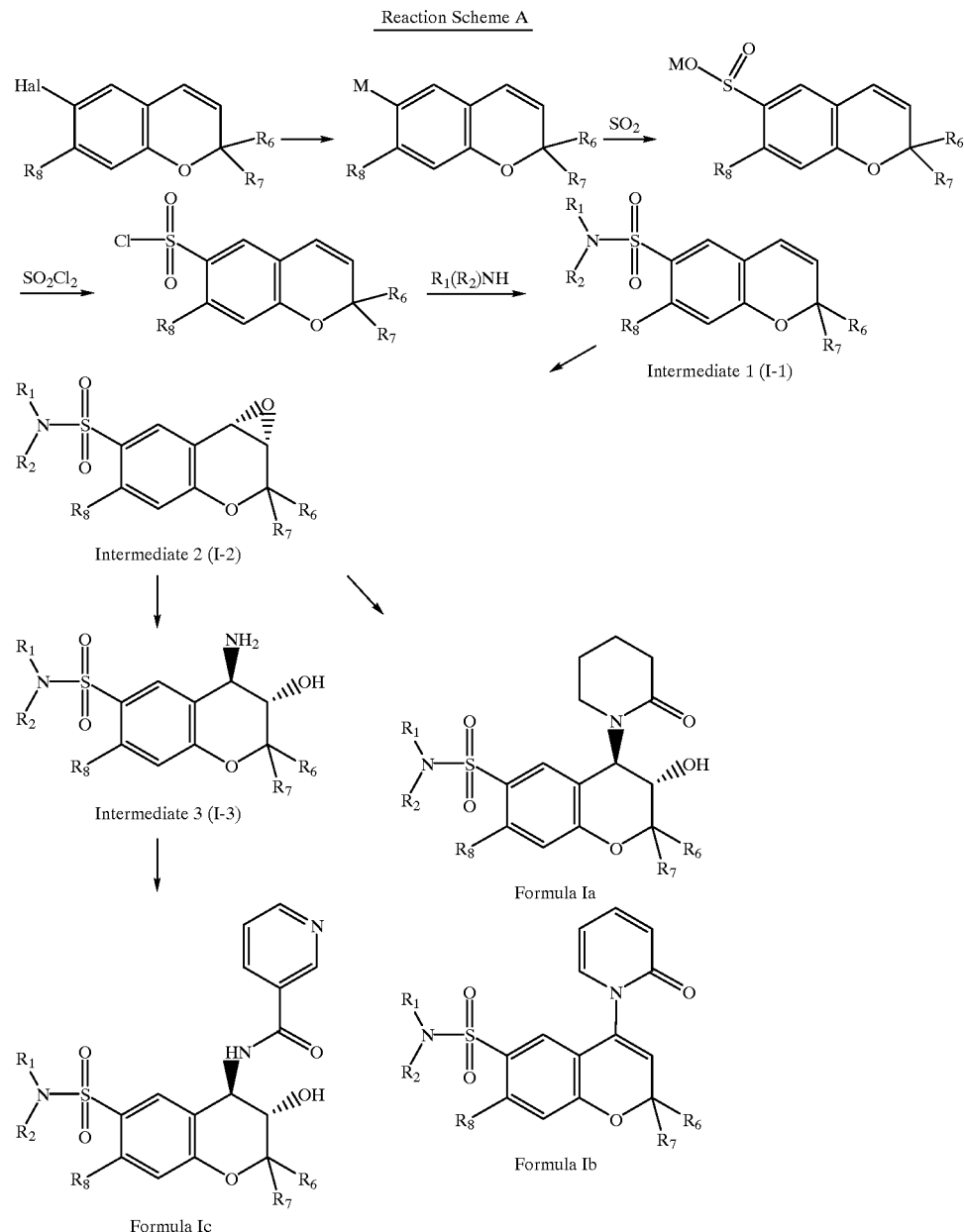

Intermediate 1 may alternatively be prepared in accordance with the following general Reaction Scheme B:

Reaction Scheme B

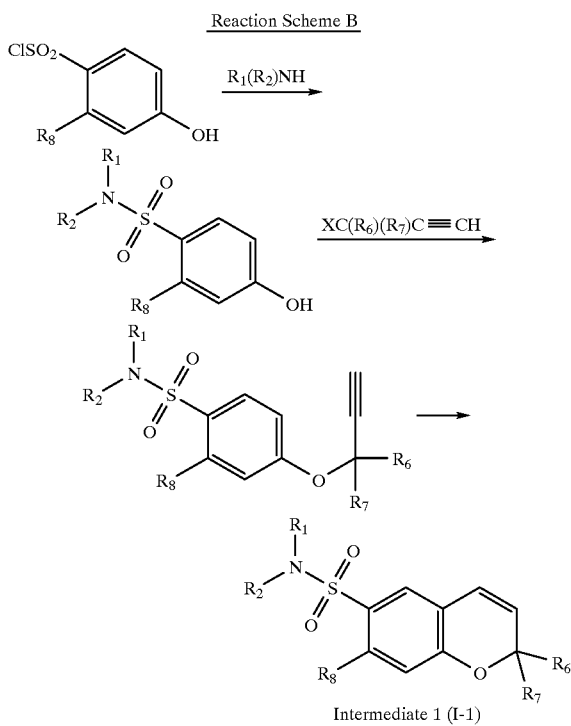

Intermediate 1 (I-1)

wherein the R groups are as defined above and X is a leaving group, for example halogen, preferably chlorine. The last step (cyclization of the ether) is carried out by heating (e.g., ca. 200° C.) in a suitable high-boiling solvent, e.g., N,N-diethylaniline or 1,2-dichlorobenzene. The formation of the ether by alkylation of the phenol compound with a compound of formula $XC(R_6)R_7)CCH$ is preferably carried out under basic conditions in the presence of a suitable catalyst, for example using an anhydrous metal carbonate (e.g., potassium carbonate) as base in an aprotic solvent (e.g., butan-2-one) in the presence of a silver catalyst compound (e.g., silver oxide), or using 1,8-diazabicyclo[5.4.0]-undec-7-ene as base in in a suitable solvent (e.g., acetonitrile) in the presence of a copper salt catalyst (e.g., copper (I) chloride).

The invention thus further provides

3) A process for the production of a benzopyran as defined under 1) above, for example a compound of formula I as defined under 2 above, or N-oxide thereof, or physiologically-hydrolysable and -acceptable ester of such a benzopyran or N-oxide or acid addition or quarternary ammonium salt of such a benzopyran, N-oxide or ester, which process comprises:

i) for the production of a benzopyran as aforesaid:

i$^1$) reacting a 1a,7b-dihydro-2,2-di($C_{1-5}$alkyl)-6-(aryl (or 2,2-dimethylpropyl) sulfonamido)-2H-oxireno[c][1] benzopyran (e.g., Intermediate 2 above) with an alkali metal salt of a carboxamide, for example a compound of formula $R_{10}$—CO—N—$R_9$ $M^+$ wherein $R_9$ and $R_{10}$ have the meanings given for formula I above and $M^+$ is a lithium, sodium or potassium ion, and optionally dehydrogenating the 3,4-dihydro-benzopyran thus obtained to obtain the corresponding benzopyran; or i$^2$) acylating and, when required, alkylating the amino group of a 2,2-di($C_{1-5}$alkyl)- or trans-2,2-di($C_{1-5}$alkyl)-3,4-dihydro-3-hydroxy-4-amino-6-(aryl (or 2,2-dimethylpropyl) sulfonamido)2H-1-benzopyran, e.g., acylating Intermediate 3 above with the appropriate acyl halide, e.g., nicotinoyl chloride; or ii) for the production of a benzopyran N-oxide or physiologically-hydrolysable and -acceptable ester of a benzopyran or benzopyran N-oxide as aforesaid, esterifying a benzopyran or benzopyran N-oxide as defined under 1) above having a free hydroxy group or moiety to introduce an appropriate ester grouping, for example reacting a compound of formula I as hereinbefore defined wherein $R_5$ is hydroxy, or N-oxide thereof, with an appropriate acid halide or anhydride, and/or oxidising a benzopyran or physiologically-hydrolysable and -acceptable ester thereof as defined under 1 above, for example oxidising a compound of formula I as hereinbefore defined or physiologically-hydrolysable and -acceptable ester thereof;

and recovering the obtained benzopyran, benzopyran N-oxide or physiologically-hydrolysable and-acceptable ester thereof in free or in acid addition or quarternary ammonium salt form.

Process step i$^1$) above may be carried out in accordance with methods known in the art, for example by reaction at from ambient temperatures to reflux in the presence of an inert solvent or diluent such as tetrahydrofuran or dimethylsulfoxide. Suitably the required alkali metal salt is preformed in situ, for example as described in Examples 1 to 13 hereinafter. By appropriate use of e.g. Na salts, both benzopyrans and dihydro-benzopyrans of the invention may be obtained. Use of lithium salts leads primarily or exclusively to the preferred dihydro-benzopyrans of the invention as illustrated in Examples 1 to 13 hereinafter.

Process step i$^2$) may also be carried out in accordance with methods known in the art. Reaction is suitably carried out at temperatures of from 0° to 100° C. in an inert solvent or diluent such as acetonitrile, dichloromethane, or dimethylformamide, preferably in the presence of an acid binding agent, e.g. trialkylamine or alkali metal carbonate. The procedure is illustrated in Examples 14 through 17 hereinafter.

Process step ii) may be carried out in accordance with conventional acylation/N-oxidation procedures, e.g. for the obtention of N-oxides by treatment with hydrogen peroxide, m-chloroperbenzoic acid or peracetic acid.

Initially obtained free bases may be converted into acid addition or quarternary ammonium salts by reaction with acids or e.g. alkyl, for example methyl, halides, and vice versa.

As will be appreciated, variants of or alternatives to the above procedures may be employed as known in the art, e.g. for the interconversion of initially obtained compounds or for the introduction of alternative carboxamido groups at the 4-position. Labile groups may be protected e.g. during acylation procedures, employing conventional protecting groups, e.g. hydroxy-protecting groups. In addition, initially obtained 3,4-dihydro-benzopyrans may, if desired, be converted to corresponding benzopyrans by dehydration across the 3,4-linkage, again in accordance with standard techniques, e.g., as described in example 19. Further alternatives will be apparent to those skilled in the art.

Intermediates 1, 2, and 3 illustrated above and in the accompanying Examples, are new, e.g., of formula I-1, I-2, and I-3

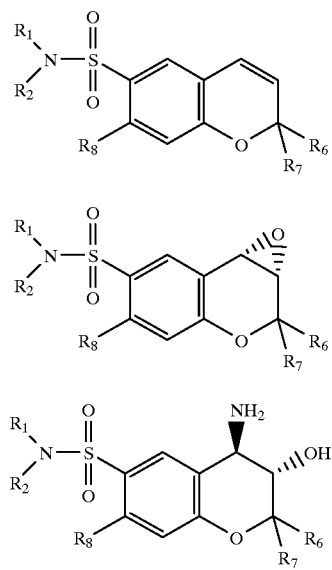

wherein $R_1$, $R_2$, $R_6$, $R_7$, and $R_8$ are as for formula I above. Such intermediates, in particular the specific Intermediates 1a through 1l, 2a through 2p, and 3a through 3g described and exemplified below, and processes for their production, also constitute part of the present invention.

PREPARATION OF INTERMEDIATES

Intermediate 1

Intermediate 1 compounds (formula I-1 supra) can be prepared following Reaction Scheme A, supra, e.g., as follows:

(1a) 1,2,3,4-Tetrahydro-1-[(2,2-dimethyl-2H-1-benzopyran-6-yl)sulphonyl]quinoline A solution of n-butyl lithium in hexane (20 mL of 1.6 M, 32 mmol) is added to a stirred solution of 6-bromo-2,2-dimethyl-2H-1-benzopyran (7.17 g, 30 mmol) in dry tetrahydrofuran (100 mL) at −78° C. under an argon atmosphere. The mixture is stirred for 1 hour at −78° C., and then a stream of sulphur dioxide gas is bubbled through the solution for 30 minutes, after which the resulting mixture is allowed to warm to 20° C. The mixture is then evaporated to dryness under reduced pressure to give a residue which is suspended in dry hexane (300 mL), cooled to 0° C. and treated dropwise with a solution of sulphuryl chloride (2.53 mL, 4.21 g, 31 mmol) in dry hexane (30 mL). The resulting mixture is stirred for 30 minutes at 0° C., followed by 60 minutes at 20° C. and then evaporated to dryness under reduced pressure to afford the crude sulphonyl chloride which is suspended in 1,1,1-trichloroethane (200 mL), treated with triethylamine (4.00 mL, 2.90 g, 29 mmol) and 1,2,3,4-tetrahydroquinoline (7.6 mL, 8.03 g, 60 mmol) and stirred at 20° C. for 16 hours. The solvent and excess reagents are evaporated off under reduced pressure to yield the crude product. This is purified by column chromatography on silica gel, eluent 5% acetone in hexane, to give the title compound as a yellow oil, having the following physical characteristics:

$^1$H-NMR (δ-CDCl$_3$): 1.42 (s, 6H), 1.69 (m, AMX, 2H), 2.49 (m, AMX, 2H), 3.78 (m, AMX, 2H), 5.65 (d, J=10.8 Hz, 1H), 6.20 (d, J=10.8 Hz, 1H), 6.71 (d, J=8.4 Hz, 1H), 7.01 (dd, 7.5 Hz, 1H), 7.06 (ddd, 1H), 7.18 (ddd, 1H), 7.20 (d, J=2.4 Hz, 1H), 7.29 (dd, J=2.4, 8.4 Hz, 1H) and 7.76 (d, J=8.6 Hz, 1H).

The following compounds are prepared analogously by utilising the appropriate amine:

(1b) 2,2-dimethyl-N-phenyl-2H-1-benzopyran-6-sulphonamide (1c) 2,2-dimethyl-N-(4-methoxyphenyl)-2H-1-benzopyran-6-sulphonamide (1d) 2,2-dimethyl-N-methyl-N-phenyl-2H-1-benzopyran-6-sulphonamide (1e) 2,2-dimethyl-N-(4-methoxyphenyl)-N-methyl-2H-1-benzopyran-6-sulphonamide (1f) 2,2-dimethyl-N-(3-methoxyphenyl)-N-methyl-2H-1-benzopyran-6-sulphonamide (1g) 2,2-dimethyl-N-(4-fluorophenyl)-N-methyl-2H-1-benzopyran-6-sulphonamide (1h) 2,2-dimethyl-N-[4-(1,1,1-trifluoromethyl)phenyl]-N-methyl-2H-1-benzopyran-6-sulphonamide (1i) 2,2-dimethyl-N-[3-(1,1,1-trifluoromethyl)phenyl]-N-methyl-2H-1-benzopyran-6-sulphonamide (1j) 2,2-dimethyl-N-methyl-N-(4-pyridyl)-2H-1-benzopyran-6-sulphonamide (1k) 2,2-dimethyl-N-methyl-N-(3-pyridyl)-2H-1-benzopyran-6-sulphonamide (1l) 2,2-dimethyl-N-ethyl-N-phenyl-2H-1-benzopyran-6-sulphonamide Intermediate 1 compounds can also be prepared following Reaction Scheme B, e.g., as follows:

(1b) 2,2-dimethyl-N-phenyl-2H-1-benzopyran-6-sulphonamide (i) 4-Hydroxy-N-phenylbenzenesulphonamide: Thionyl chloride (109 mL, 1.5 M) is added dropwise over 25 minutes to a stirred mixture of sodium 4-hydroxybenzenesulphonate (69.7 g, 300 mmol) and dimethylformamide (1.5 mL) in 1,2-dichloroethane (400 mL). The resulting mixture is stirred at 80° C. for 12 hours, cooled to <20° C., poured onto ice-water (1000 mL) and extracted with 1,2-dichloroethane (3×100 mL). The combined extracts are dried (Na$_2$SO$_4$) and filtered. The resulting solution of 4-hydroxybenzenesulphonyl chloride is treated with aniline (69 mL, 750 mmol) and then stirred at 80° C. for 2 hours. The mixture is then washed with hydrochloric acid (4×200 mL of 2 M), dried (Na$_2$SO$_4$), filtered and the solvent is evaporated off under reduced pressure to yield the crude product which is purified by recrystallisation from ether-cyclohexane to give the title compound as a pale-yellow crystalline solid, m.p. 140–141° C.

Other phenol intermediates for use in Reaction Scheme B are prepared analogously by utilising the appropriate amine, e.g., 4-Hydroxy-N-methyl-N-phenylbenzenesulphonamide, m.p. 151–152° C.

1,2,3,4-Tetrahydro-2-(4-hydroxyphenylsulphonyl)quinoline, m.p. 119–120° C.

These phenol intermediates are then O-alkylated and cyclized, e.g., as follows:

(ii) 2,2-dimethyl-N-phenyl-2H-1-benzopyran-6-sulphonamide Copper(I)chloride (0.44 g, 4.4 mmol) is added to a stirred suspension of N-phenyl 4-hydroxybenzenesulphonamide (110.5 g, 443 mmol) in dry acetonitrile (1660 mL) at 0° C. under an argon atmosphere. The mixture is stirred for 15 minutes at 0° C. and then treated dropwise over 30 minutes with 1,8-diazabicyclo[5.4.0]undec-7-ene (78.1 mL, 523 mmol). After a further 30 minutes at 0° C. the suspension is treated dropwise with 3-chloro-3-methyl-1-butyne (50 g, 487 mmol) and stirred for an additional 2 hours at 0° C. and for 18 hours at 20° C. The resulting mixture is evaporated to dryness under reduced pressure to give a residue which is treated with hydrochloric acid (1000 mL of 1.0 M) and extracted with ethyl acetate (3×500 mL). The combined extracts are dried (Na$_2$SO$_4$), filtered and the solvent is evaporated off under reduced pressure to yield crude N-phenyl-4-(1,1-dimethyl-2-propynyl)oxybenzenesulphonamide. This is dissolved in N,N-diethylaniline (100 mL) and added dropwise with stirring over 60 minutes to N,N-diethylaniline (200 mL) at 200° C. After an additional 1 hour at 200° C., the reaction mixture is cooled to room temperature, diluted with ethyl acetate (1000 mL) and with washed with hydrochloric acid (5×800 mL). The ethyl acetate solution is dried (Na$_2$SO$_4$), filtered and the solvent is evaporated off under reduced pressure to yield the crude product. This is purified by chromatography on silica gel, eluent 10% ethyl acetate in hexane and recrystallised from ether-hexane to give the title compound as a colourless crystalline solid, m.p. 91–93° C.

Other Intermediate 1 compounds of formula I-1 are prepared analogously from the corresponding phenol compounds prepared from the corresponding amines analogously to step (i).

Intermediate 2

(2a) 1,2,3,4-Tetrahydro-1-[(1a,7b-dihydro-2,2-dimethyl-2H-oxireno[c][1]benzopyran-6-yl)sulphonyl]quinoline N-Bromosuccinimide (3.65 g, 20.5 mmol) is added to a stirred solution of Intermediate 1a (6.80 g, 19.1 mmol) in dimethylsulphoxide (70 mL) and water (0.89 g, 0.50 mmol) at 15° C. The mixture is stirred for 2 hours and then treated with a solution of sodium hydroxide (4.0 g, 100 mmol) in dioxan-water and stirred at 20° C. for 30 minutes. The mixture is concentrated to 25% volume by evaporation under reduced pressure, treated with saturated aqueous ammonium chloride solution (300 mL) and extracted with ethyl acetate (2×200 mL). The combined extracts are dried (Na$_2$SO$_4$), filtered and the solvent is evaporated off under reduced pressure to yield the crude product which is purified by column chromatography (silica gel, 10% acetone in hexane) to give the title compound as a yellow oil, having the following physical characteristics:

$^1$H-NMR (δ-CDCl$_3$): 1.24 (s, 3H), 1.56 (s, 3H), 1.68 (m, AMX, 2H), 2.47 (m, AMX, 2H), 3.50 (d, J=6.0 Hz, 1H), 3.79 (m, AMX, 2H), 3.84 (d, J=6.0 Hz, 1H), 6.76 (d, J=8.5 Hz, 1H), 6.98 (d, J=7.5 Hz, 1H), 7.05 (ddd, 1H), 7.19 (ddd, 1H), 7.43 (dd, J=2.3, 8.5 Hz, 1H), 7.61 (d, J=2.3 Hz, 1H) and 7.78 (d, J=8.3 Hz, 1H).

The following compounds are prepared analogously by utilising the appropriate benzopyran-6-sulphonamide:

(2b) 1a,7b-Dihydro-2,2-dimethyl-N-phenyl-2H-oxireno[c][1]benzopyran-6-sulphonamide from Intermediate 1b.

(2c) 1a,7b-Dihydro-2,2-dimethyl-N-(4-methoxyphenyl)-2H-oxireno[c][1]benzopyran-6-sulphonamide from Intermediate 1c.

(2d) 1a,7b-Dihydro-2,2-dimethyl-N-methyl-N-phenyl-2H-oxireno[c][1]benzopyran-6-sulphonamide from Intermediate 1d.

(2e) 1a,7b-Dihydro-2,2-dimethyl-N-(4-methoxyphenyl)-N-methyl-2H-oxireno[c][1]benzopyran-6-sulphonamide from Intermediate 1e.

(2f) 1a,7b-Dihydro-2,2-dimethyl-N-(3-methoxyphenyl)-N-methyl-2H-oxireno[c][1]benzopyran-6-sulphonamide from Intermediate 1f.

(2g) 1a,7b-Dihydro-2,2-dimethyl-N-(4-fluorophenyl)-N-methyl-2H-oxireno[c][1]benzopyran-6-sulphonamide from Intermediate 1g.

(2h) 1a,7b-Dihydro-2,2-dimethyl-N-[4-(1,1,1-trifluoromethyl)phenyl]-N-methyl-2H-oxireno[c][1]benzopyran-6-sulphonamide from Intermediate 1h.

(2i) 1a,7b-Dihydro-2,2-dimethyl-N-[3-(1,1,1-trifluoromethyl)phenyl]-N-methyl-2H-oxireno[c][1]benzopyran-6-sulphonamide from Intermediate 1i.

(2j) 1a,7b-Dihydro-2,2-dimethyl-N-methyl-N-(4-pyridyl)-2H-oxireno[c][1]benzopyran-6-sulphonamide from Intermediate 1j.

(2k) 1a,7b-Dihydro-2,2-dimethyl-N-methyl-N-(3-pyridyl)-2H-oxireno[c][1]benzopyran-6-sulphonamide from Intermediate 1k.

(2l) 1a,7b-Dihydro-2,2-dimethyl-N-ethyl-N-phenyl-2H-oxireno[c][1]benzopyran-6-sulphonamide from Intermediate 1l.

(2m) (3S, 4S)-1,2,3,4-Tetrahydro-1-[(1a,7b-dihydro-2,2-dimethyl-2H-oxireno[c][1]benzopyran-6-yl)sulphonyl]quinoline A mixture of aqueous sodium hypochlorite (300 mL of 14%) and aqueous sodium phosphate, dibasic (130 mL of 0.5 M) is added dropwise, over 3 hours to a stirred mixture of Intermediate 1a (30.0 g, 84.4 mmol) and (S,S)-(+)-N,N'-bis(3,5-di-tert-butylsalicylidene)-1,2-cyclohexanediaminomanganese(III)chloride (4.0 g, 7.3 mmol) in isopropylacetate (300 mL) at 50° C. The mixture is stirred for an additional 4 hours, filtered and extracted with ethyl acetate (2×500 mL). The combined extracts are dried (Na$_2$SO$_4$), filtered and the solvent is evaporated off under reduced pressure to yield the crude product which is purified by chromatography on silica gel, eluent 10–50% ethyl acetate in hexane, to give the title compound as a yellow oil.

The following compounds are prepared analogously by utilising the appropriate intermediate compound:

(2n) (3S, 4S)-N-Methyl-N-phenyl-[1a,7b-dihydro-2,2-dimethyl-2H-oxireno[c][1]benzopyran-6-sulphonamide] from Intermediate 1d; $[\alpha]_D^{20}$=−25.4° (c=1.00, DMF).

(2o) (3R, 4R)-N-Methyl-N-phenyl-[1a,7b-dihydro-2,2-dimethyl-2H-oxireno[c][1]benzopyran-6-sulphonamide] from Intermediate 1d and (R,R)-(−)-N,N'-bis(3,5-di-tert-butylsalicylidene)-1,2-cyclohexanediaminomanganese(III)chloride in lieu of (S,S)-(+)-N,N'-bis(3,5-di-tert-butylsalicylidene)-1,2-cyclohexanediaminomanganese(III)chloride.

(2p) (3R, 4R)-1,2,3,4-Tetrahydro-1-[(1a,7b-dihydro-2,2-dimethyl-2H-oxireno[c][1]benzopyran-6-yl)sulphonyl]quinoline, prepared as for 2m using Intermediate 1a and (R,R)-(+)-N,N'-bis(3,5-di-tert-butylsalicylidene)-1,2-cyclohexanediaminomanganese(III)chloride to give the title compound having an optical rotation of $[\alpha]_D^{20}$=+24.4° (c=1.00, DMF).

Intermediate 3

(3a) trans-1,2,3,4-Tetrahydro-1-[(4-amino-3,4-dihydro-2,2-dimethyl-3-hydroxy-2H-1-benzopyran-6-yl)sulphonyl]quinoline Intermediate 2a (3.49 g, 9.4 mmol) is treated with a saturated solution of ammonia in ethanol (60 mL) and heated at 90° C. in an autoclave for 15 hours. The solvent is evaporated off under reduced pressure to yield the crude product which is purified by chromatography on silica gel, eluent 25% aqueous NH$_3$—MeOH—tBuOMe (1:5:94) to give the title compound as a foam, having the following physical characteristics:

$^1$H-NMR (δ-CDCl$_3$): 1.18 (s, 3H), 1.50 (s, 3H), 1.66 (m, AMX, 2H), 2.42 (m, AMX, 2H), 3.26 (d, J=9.9 Hz, 1H), 3.52 (d, J=9.9 Hz), 3.79 (m, AMX, 2H), 6.76 (d, J=8.5 Hz, 1H), 6.99 (d, J=7.5 Hz, 1H), 7.07 (ddd, 1H), 7.20 (ddd, 1H), 7.42 (dd, J=2.3, 8.5 Hz, 1H), 7.44 (m, 1H) and 7.81 (d, J=8.3 Hz, 1H).

The following compounds are prepared analogously by utilising the appropriate epoxide:

(3b) trans-N-Methyl-N-phenyl-(4-amino-3,4-dihydro-2,2-dimethyl-2H-1-benzopyran)-6-sulphonamide from Intermediate 2d.

(3c) trans-N-Ethyl-N-phenyl-(4-amino-3,4-dihydro-2,2-dimethyl-2H-1-benzopyran)-6-sulphonamide from Intermediate 2l.

(3d) (3S, trans)-1,2,3,4-Tetrahydro-1-[(4-amino-3,4-dihydro-2,2-dimethyl-3-hydroxy-2H-1-benzopyran-6-yl)sulphonyl]quinoline from Intermediate 2m; $[\alpha]_D^{20}$=+33.2° (c=1.00, DMF).

(3e) (3S, trans)-N-Methyl-N-phenyl-(4-amino-3,4-dihydro-2,2-dimethyl-2H-1-benzopyran)-6-sulphonamide from Intermediate 2n; $[\alpha]_D^{20}$=+29.2° (c=1.00, DMF).

(3f) (3R, trans)-N-Methyl-N-phenyl-(4-amino-3,4-dihydro-2,2-dimethyl-2H-1-benzopyran)-6-sulphonamide from Intermediate 2o.

(3g) (3R, trans)-1,2,3,4-Tetrahydro-1-[(4-amino-3,4-dihydro-2,2-dimethyl-3-hydroxy-2H-benzopyran-6-yl)sulphonyl]quinoline from Intermediate 2p; $[\alpha]_D^{20}$=−25.0° (c=1.00, DMF).

EXAMPLE 1

Production of trans-1,2,3,4-Tetrahydro-1-[[3,4-dihydro-2,2-dimethyl-3-hydroxy-4-(2-oxo-piperidin-1-yl)-2H-1-benzopyran-6-yl]sulphonyl]quinoline (i.e. a compound of formula I wherein $R_1$ is phenyl and $R_2$ is trimethylene linked to $R_1$ to form a 1,2,3,4-tetrahydroquinolin-1-yl moiety; $R_3$ is a group of formula —N($R_9$)—$COR_{10}$ wherein $R_9$ and $R_{10}$ together represent a group of formula —$(CH_2)_n$— in which n is 4; $R_4$ is hydrogen and $R_5$ is hydroxy in the trans position with respect to $R_3$; $R_6$ and $R_7$ are methyl; and $R_8$ is hydrogen).

A stirred solution of anhydrous 2-piperidinone (1.00 g, 10 mmol) in dry tetrahydrofuran (50 mL) at 0° C. under an argon atmosphere is treated with a solution of lithium bis(trimethylsilyl)amide in tetrahydrofuran (10 mL of 1.0M, 10 mmol) and stirred at 20° C. for 2 hours. The resulting suspension is treated with a solution of 1,2,3,4-Tetrahydro-1-[(1a,7b-dihydro-2,2-dimethyl-2H-oxireno[c][1]benzopyran-6-yl) sulphonyl]quinoline (Intermediate 2a; 1.86 g, 5 mmol) in dry tetrahydrofuran (20 mL) and heated at 80° C. for 17 hours. The mixture is cooled to 15° C., treated with a saturated aqueous solution of ammonium chloride (100 mL). The precipitated product is filtered, washed with water, dried and recrystallised from ethanol to give the title compound as a colourless crystalline solid, m.p. 290–292° C.

The following compounds having different $R_1$ and $R_2$ groups and the same $R_3$–$R_{10}$ groups as for example 1 are prepared analogously by utilising the appropriate epoxide intermediates:

| Example | $R_1$ | $R_2$ | Epoxide Intermediate | m.p. (°C.) |
| --- | --- | --- | --- | --- |
| 2 | phenyl | H | 2b | 238–240 |
| 3 | 4-methoxyphenyl | H | 2c | 237–239 |
| 4 | phenyl | methyl | 2d | 262–264 |
| 5 | 4-methoxyphenyl | methyl | 2e | 244–246 |
| 6 | 3-methoxyphenyl | methyl | 2f | 218–220 |
| 7 | 4-fluorophenyl | methyl | 2g | 245–245 |
| 8 | 4-trifluoromethylphenyl | methyl | 2h | 230–232 |
| 9 | 3-trifluoromethylphenyl | methyl | 2l | 219–221 |
| 10 | 4-pyridyl | methyl | 2j | 213–214 |
| 11 | 3-pyridyl | methyl | 2k | 260–261 |
| 12 | phenyl | ethyl | 2l | 189–190 |

EXAMPLE 13

Production of trans-[3,4-Dihydro-2,2-dimethyl-3-hydroxy-6-[(1,2,3,4-tetrahydroquinolin-1-yl)sulphonyl]-2H-1-benzopyran-4-yl]-3-pyridinecarboxamide (i.e., the compound of formula I wherein $R_1$ is phenyl and $R_2$ is trimethylene linked to $R_1$ to form a 1,2,3,4-tetrahydroquinolin-1-yl moiety; $R_3$ is a group of formula —N($R_9$)—$COR_{10}$ wherein $R_9$ is H and $R_{10}$ is pyridyl; $R_4$ is hydrogen and $R_5$ is hydroxy in the trans position with respect to $R_3$; $R_6$ and $R_7$ are methyl; and $R_8$ is hydrogen).

A stirred solution of trans-1,2,3,4-tetrahydro-1-[(4-amino-3,4-dihydro-2,2-dimethyl-3-hydroxy-2H-1-benzopyran-6-yl)sulphonyl]quinoline (Intermediate 3a; 1.00 g, 2.6 mmol), triethylamine (0.80 mL, 0.58 g, 5.7 mmol) and 4-dimethylaminopyridine (0.081 g, 0.67 mmol) in dry dimethylformamide (50 mL) under an argon atmosphere, is treated with nicotinoyl chloride, hydrochloride (0.51 g, 2.8 mmol) and stirred at 18° C. for 20 hours. The solvent is evaporated off under reduced pressure to yield the crude product which is purified by chromatography on silica gel, eluent 25% aqueous $NH_3$—MeOH—tBuOMe (1:2:97) and recrystallised from tetrahydrofuran-hexane to give the title compound as a colourless crystalline solid, m.p. 217–219° C.

The following examples 14–16 having different substituents at $R_1$ and $R_2$ and the same $R_3$–$R_{10}$ groups are prepared analogously by utilising the appropriate aminoalcohol:

EXAMPLE 14 trans-[3,4-Dihydro-2,2-dimethyl-6-[(N-methyl-N-phenylamino)sulphonyl]-3-hydroxy-2H-1-benzopyran-4-yl]-3-pyridinecarboxamide, m.p. 238–240° C., from Intermediate 3b.

EXAMPLE 15 trans-[3,4-Dihydro-2,2-dimethyl-6-[(N-ethyl-N-phenylamino)sulphonyl]-3-hydroxy-2H-1-benzopyran-4-yl]-3-pyridinecarboxamide, m.p. 232–233° C., from Intermediate 3c.

EXAMPLE 16

Production of trans-N-Methyl-N-phenyl-3,4-dihydro-4-(1,2-dihydro-2-oxo-1-pyridyl)-2,2-dimethyl-3-hydroxy-2H-1-benzopyran-6-sulphonamide (i.e. a compound of formula I wherein $R_1$ is phenyl, $R_2$ is methyl, $R_3$ is a group of formula —N($R_9$)—$COR_{10}$ wherein $R_9$ and $R_{10}$ together are 1,3-butadienylene, $R_4$ is hydrogen, $R_5$ is hydroxy in the trans position with respect to $R_3$, $R_6$ and $R_7$ are methyl, and $R_8$ is hydrogen).

A stirred solution of Intermediate 2d (2.48 g, 7.2 mmol) in dry isopropanol (50 mL), containing pyridine (3 mL) is treated with 2-hydroxypryridine (1.64 g, 13.2 mmol) and heated at 110° C. for 18 hours. The solvent is evaporated off under reduced pressure to yield the crude product which is purified by chromatography on silica gel, eluent 10% ethanol in toluene and recrystallised from isopropanol-cyclohexane to give the title compound as a colourless crystalline solid m.p. 251–254° C. and having the following physical characteristics:

$^1$H-NMR (δ-d$^6$ DMSO), 120° C.): 1.26 (s, 3H), 1.48 (s, 3H), 3.00 (s, 3H), 4.18 (br.s, 1H), 5.48 (br, d, 1H), 5.70 (br.s, 1H), 6.1 (dd, 1H), 6.19 (ddd, 1H), 6.27 (dd, 1H), 6.39 (dd, 1H), 6.91 (d, 1H), 7.00 (dd, 1H), 7.18–7.43 (m, 5H).

EXAMPLE 17

Production of N-Methyl-N-phenyl-4-(1,2-dihydro-2-oxo-1-pyridyl)-2,2-dimethyl-2H-1-benzopyran-6-sulphonamide (i.e., a compound of formula I as for example 16 except for $R_4$ and $R_5$ which together form a double bond).

A stirred mixture of the compound of Example 16 (1.17 g, 2.65 mmol), and sodium hydroxide on a support (0.8–1.6 mm, 14–25 mesh ASTM; Cat. No. 1567, E.Merck; 1.17 g) in dry dioxan (50 mL) is heated at 110° C. for 30 minutes under an argon atmosphere. The solution is filtered and the solvent is evaporated off under reduced pressure to yield the crude product which is purified by chromatography on silica gel, eluent 5% ethanol in toluene and recrystallised from dichloromethane-pentane to give the title compound as a cream crystalline solid, m.p. 179–181° C.

When desired, compounds of the invention can be prepared in optically active form as illustrated by Examples 18–22:

EXAMPLE 18

Production of (3S, trans)-N-Methyl-N-phenyl-3,4-dihydro-4-(1,2-dihydro-2-oxo-1-pyridyl)-2,2-dimethyl-3-hydroxy-2H-1-benzopyran-6-sulphonamide A stirred solution of (3S, 4S)-N-methyl-N-phenyl-[1a,7b-dihydro-2,2-dimethyl-2H-oxireno[c][1]benzopyran-6-sulphonamide] (Intermediate 2n; 2.80 g, 8.1 mmol) in dry isopropanol (28 mL), containing pyridine (1.5 mL) is treated with 2-hydroxypyridine (1.54 g, 16.2 mmol) and heated at 90° C. for 18 hours. The solvent is evaporated off under reduced pressure to yield the crude product which purified by chromatography on silica gel, eluent 25% ethyl acetate in cyclohexane and recrystallised from t-butyl methyl ether-ethyl acetate to give the title compound as a colourless crystalline solid, m.p. 262–265° C., $[\alpha]_D^{20}$=−130.2° (c=1.00, DMF).

EXAMPLE 19

Production of (3S, trans)-[3,4-Dihydro-2,2-dimethyl-6-[(N-methyl-N-phenylamino)sulphonyl]-3-hydroxy-2H-1-benzopyran-4-yl]-3-pyridinecarboxamide A stirred solution of (3S, trans)-N-Methyl-N-phenyl-(4-amino-3,4-dihydro-2,2-dimethyl-2H-1-benzopyran)-6-sulphonamide (Intermediate 3e, 3.12 g, 8.61 mmol), triethylamine (4.0 mL, 2.90 g, 28.6 mmol) and 4-dimethylaminopyridine (0.312 g. 2.55 mmol) in dry dichloromethane (86 mL) under an argon atmosphere, is treated with nicotinoyl chloride, hydrochloride (1.61 g, 9.04 mmol) and stirred at 18° C. for 20 hours. The solvent is then evaporated off under reduced pressure to yield a mixture which is then treated with aqueous ammonia (100 mL of 0.05 M) and extracted with 10% ethanol in ethyl acetate (3×100 mL). The combined extracts are dried ($Na_2SO_4$), filtered and the solvent is evaporated off under reduced pressure to yield the crude product which purified by recrystallisation from ethyl acetate-diethyl ether to give the title compound as a colourless crystalline solid, m.p. 210–212° C. $[\alpha]_D^{20}$=−41.7° (c=1.00, DMF).

The following compounds are prepared analogously by utilising the appropriate amine intermediate:

EXAMPLE 20

(3R,trans)-[3,4-Dihydro-2,2-dimethyl-6-[(N-methyl-N-phenylamino)sulphonyl]-3-hydroxy-2H-1-benzopyran-4-yl]-3-pyridinecarboxamide from intermediate 3f; m.p. 177–180° C., $[\alpha]_D^{20}$=+43.4° (c=1.00, DMF).

EXAMPLE 21

(3S,trans)-[3,4-Dihydro-2,2-dimethyl-3-hydroxy-6-[(1,2,3,4-tetrahydroquinolin-1-yl)sulphonyl]-2H-1-benzopyran-4-yl]-3-pyridinecarboxamide from intermediate 3d; m.p. 199–205° C., $[\alpha]_D^{20}$=−58.0° C. (c=1.00, DMF).

EXAMPLE 22

(3R, trans)-[3,4-Dihydro-2,2-dimethyl-3-hydroxy-6-[(1,2,3,4-tetrahydroquinolin-1-yl)sulphonyl]-2H-1-benzopyran-4-yl]-3-pyridinecarboxamide from intermediate 3g; m.p. 199–202° C., $[\alpha]_D^{20}$=+58.1° (c=1.00, DMF).

EXAMPLE 23

Production of (3S, trans)-N-Phenyl-3,4-dihydro-3-hydroxy-2,2-dimethyl-4-(2-oxo-1-piperidinyl)-2H-1-benzopyran-6-sulphonamide (23a) [3,4-Dihydro-2,2-dimethyl-2H-1-benzopyran-6-sulphonyl]phenylcarbamic acid, 1,1-dimethylethyl ester A stirred solution of 2,2-dimethyl-N-phenyl-2H-1-benzopyran-6-sulphonamide (Intermediate 1b; 6.30 g, 20 mmol) and 4-dimethylaminopyridine (200 mg, 1.6 mmol) in acetonitrile (60 mL) is treated with di-t-butyl dicarbonate (4.81 g, 22 mmol) and stirred at 18° C. for 2 hours. The solvent is evaporated off under reduced pressure to give a residue which is treated with aqueous sodium hydrogen carbonate (200 mL of 2M) and extracted with ethyl acetate (2×100 mL). The combined extracts are dried ($Na_2SO_4$), filtered and the solvent is evaporated off under reduced pressure to yield the product which is recrystallised from t-butylmethyl ether-hexane to give the title compound as a colourless crystalline solid, m.p. 117–120° C.

(23b) (3S,4S)-[1a,7b-Dihydro-2,2-dimethyl-2H-oxireno[c][1]benzopyran-6-sulphonyl]phenylcarbamic acid, 1,1-dimethylethyl ester A mixture of aqueous sodium hypochlorite (26 mL of 14%) and aqueous sodium phosphate, dibasic (40 mL of 0.05 M) is added to a stirred mixture of [3,4-dihydro-2,2-dimethyl-2H-1-benzopyran-6-sulphonyl]phenylcarbamic acid, 1,1-dimethylethyl ester (5.46 g, 13.1 mmol) and (S,S)-(+)-N,N'-bis(3,5-di-tert-butylsalicylidene)-1,2-cyclohexanediaminomanganese(III)chloride (0.54 g, 1.0 mmol) in isopropylacetate (40 mL) at 17° C. The mixture is stirred for 30 minutes, diluted with saturated aqueous sodium chloride (200 mL), filtered and extracted with ethyl acetate (3×300 mL). The combined extracts are dried ($Na_2SO_4$), filtered and the solvent is evaporated off under reduced pressure to yield the crude product which is purified by chromatography on silica gel, eluent 10% ethyl acetate in cyclohexane and recrystallised from ethyl acetate-hexane to give the title compound as a colourless crystalline solid, m.p. 148–150° C., $[\alpha]_D^{20}$=−35.0° (c=1.00, DMF).

(23c) (3S, trans)-N-Phenyl-3,4-dihydro-3-hydroxy-2,2-dimethyl-4-(2-oxo-1-piperidinyl)-2H-1-benzopyran-6-sulphonamide A stirred solution of anhydrous-2-piperidinone (9.92 g, 100 mmol) in dry tetrahydrofuran (100 mL) at 0° C. under an argon atmosphere is treated with a solution of lithium bis(trimethylsilyl)amide in tetrahydrofuran (100 mL of 1.0 M, 100 mmol) and stirred at 20° C. for 2 hours. The resulting suspension is treated with a solution of (3S,4S)-[1a,7b-dihydro-2,2-dimethyl-N-phenyl-2H-oxireno[c][1]benzopyran-6-sulphonyl]phenylcarbamic acid, 1,1-dimethylethyl ester (7.20 g, 16.7 mmol) in dry tetrahydrofuran (35 mL) and heated at 50° C. for 17 hours. The mixture is cooled to 15° C., treated with a saturated aqueous solution of ammonium chloride (400 mL) and extracted with ethyl acetate (2×200 mL). The combined extracts are dried ($Na_2SO_4$), filtered and the solvent is evaporated off under reduced pressure to yield the crude product which is purified by recrystallisation from ethanol-ethyl acetate to give the title compound as a colourless crystalline solid, m.p. 272–276° C., $[\alpha]_D^{20}$=−92.0° (c=1.00, DMF).

EXAMPLE 24

Production of (3R, trans)-N-phenyl-3,4-Dihydro-3-hydroxy-2,2-dimethyl-4-(2-oxo-1-piperidinyl)-2H-1-benzopyran-6-sulphonamide (24a) (3R, 4R)-[1a,7b-dihydro-2,2-dimethyl-2H-oxireno[c][1]-benzopyran-6-sulphonyl]phenylcarbamic acid, 1,1-dimethylethyl ester Utilising the procedure described in Example 23b but employing (R,R)-(+)-N,N'-bis(3,5-di-tert-butylsalicylidene)-1,2-cyclohexanediaminomanganese (III) chloride in place of (S,S)-(+)-N,N'-bis(3,5-di-tert-butylsalicylidene)-1,2-cyclohexanediaminomanganese (III) chloride affords the title compound as a colourless crystalline solid, m.p. 146–148° C., $[\alpha]_D^{20}$=+34.9° (c=1.00, DMF).

(24b) (3R, trans)-N-Phenyl-3,4-Dihydro-3-hydroxy-2,2-dimethyl-4-(2-oxo-1-piperidinyl)-2H-1-benzopyran-6-sulphonamide Utilising the procedure described in Example 23c but employing (3R,4R)-[1a,7b-dihydro-2,2-dimethyl-2H-oxireno[c][1]benzopyran-6-sulphonyl]phenylcarbamic acid, 1,1-dimethylethyl ester in place of (3S,4S)-[1a,7b-Dihydro-2,2-dimethyl-2H-oxireno[c][1]benzopyran-6-sulphonyl]phenylcarbamic acid, 1,1-dimethylethyl ester affords the title compound as a colourless crystalline solid, m.p. 272–276° C., $[\alpha]_D^{20}$=+90.6° (c=1.00, DMF).

Benzopyrans and dihydrobenzopyrans as defined under 1. above, for example compounds of formula I as hereinbefore defined, and their N-oxides, and physiologically-hydrolysable and -acceptable esters thereof, as well as pharmaceutically acceptable acid addition and quarternary ammonium salts of said benzopyrans/dihydrobenzopyrans/N-oxides/esters, (hereinafter collectively AGENTS OF THE INVENTION) are useful as pharmaceuticals.

AGENTS OF THE INVENTION possess smooth muscle relaxant activity and exhibit potassium channel opening activity in relation to the plasmalemma membrane as demonstrated by their influence at concentrations in the region of 1 to 500 nM on various smooth muscle preparations in accordance with or analogously to the methods described in Quast, Brit. J. Pharmac., 91, 569–578 (1987). AGENTS OF THE INVENTION are thereby characterised as K$^+$ channel opening agents. AGENTS OF THE INVENTION are accordingly useful for the treatment of conditions or disorders for which therapy employing a K$^+$ channel opening agent is indicated. Therapeutic utility as K$^+$ channel opening agents may further be demonstrated in standard pharmacological tests, e.g. of cardio-vascular activity, in vitro or in vivo. Thus influence on blood-pressure may be demonstrated in the anaesthetised, cannulated normotensive rat following intra-duodenal administration 1 hr post cannulation. Anti-ischemic activity may be demonstrated in accordance with the methods described in Hof et al., Circ. Res., 62, 679 (1988). AGENTS OF THE INVENTION are accordingly useful, e.g. as smooth muscle relaxants, in particular for use as vasodilating agents, for example for the treatment of hypertension or chronic cardiac insufficiency. They are further useful as anti-ischaemic and anti-vasospastic agents, e.g. for use in the treatment of disturbed blood supply, for example to the heart, skeletal muscle or brain. They are thus useful e.g. for the treatment of angina pectoris, myocardial ischaemia or myocardial infarction; as antifibrillatory agents; for the treatment of disorders of peripheral circulation, e.g. claudicatio intermittens, Morbus Raynaud or venous ulcer; as well as for the treatment, including prophylaxis, of cerebral ischaemia, senile dementia, stroke, subarachnoidal hemorrhage and other related or consequential diseases or disorders.

AGENTS OF THE INVENTION are yet further indicated for use as gastro-intestinal, uterine and urinary tract antispastic agents, e.g. for the treatment of irritable bowel disease, diarrhea, diverticulitis, danger of miscarriage following premature labour and urinary incontinence.

AGENTS OF THE INVENTION are yet further indicated for use as hair-growth stimulating agents, e.g. for the treatment of hair loss due to ageing, e.g. male alopecia or pattern baldness, or disease-related hair loss for example consequent to infection or disturbance of the immune system, e.g., following cancer chemotherapy or radiation therapy.

Suitable dosages for such use will of course vary, e.g. depending on the particular condition to be treated, the particular AGENT OF THE INVENTION employed the mode of administration and the effect desired. In general however, a suitable oral daily dosage, e.g. for anti-hypertensive uses, will be from about 0.03 to about 2.0 mg/kg and for, e.g. anti-ischemic uses, from about 0.015 to about 0.3 mg/kg. For larger mammals, e.g. humans, an indicated oral daily dosage will thus be from about 2 to about 150 mg for anti-hypertensive uses, or from about 1 to about 20 mg for anti-ischemic uses, administered once or in divided doses 2× daily. Oral dosage forms for use in the above indications will thus suitably comprise from about 0.5 or 1.0 to about 20 or 150 mg AGENT OF THE INVENTION together with a pharmaceutically acceptable diluent or carrier therefor.

For use as hair-growth stimulating AGENTS OF THE INVENTION will appropriately be applied topically, e.g. in an appropriate cream, gel or emulsion base of the like as known in the art.

More importantly it has in accordance with the present invention been found that AGENTS OF THE INVENTION possess anti-bronchospastic activity and inhibit or reverse airways hyperreactivity. In contrast to other potassium channel activators, AGENTS OF THE INVENTION do not exhibit cardiovascular side effects following inhalation at dosages sufficient to inhibit or reverse airways hyperreactivity and relieve or prevent bronchoconstriction. These activities may be demonstrated in pharmacological test models, for example as follows:

TEST 1. REDUCTION OF AIRWAYS REACTIVITY a. In the Guinea Pig

The acute injection of pre-formed immune complex renders guinea pigs hyperreactive to histamine. Doses of histamine which cause only a small degree of bronchoconstriction prior to administration of immune complex cause a much stronger effect thereafter. Anti-hyperreactive and cardiovascular effects are measured simultaneously to determine a therapeutic window for use of the test compounds in reversal of airways hyperreactivity.

Guinea-pigs (Dunkin-Hartley, male, 400–600 g) are anaesthetised with phenobarbital (100 mg/kg i.p.) and pentobarbital (30 mg/kg i.p.) and paralysed with gallamine (10 mg/kg i.m.) and ventilated with a mixture of air and oxygen (45:55), v/v). Animals are ventilated (8 ml/kg, 1 Hz) via a tracheal cannula. Blood pressure and heart rate are recorded from the carotid artery. Ventilation is monitored by a flow transducer. When making measurements of flow, coincident pressure changes in the thorax are monitored directly via an intrathoracic trochar, permitting display of differential pressure relative to the trachea. From this information resistance and compliance are calculated at each inspiration.

An allergic reaction is initiated by intravenous injection of preformed immune complexes (prepared by adding 30 μg of bovine gamma globulin in 0.05 ml of saline to 0.05 ml of guinea pig anti-bovine gamma globulin anti-serum) 3 times at 10 minute intervals. Intravenous injections of histamine (1.0–3.2 µg/kg at 10 minute intervals) were used to define the sensitivity of the airways prior to and following the last exposure to the immune complex. Airways hyperreactivity is expressed as the paired difference for the maximal value of lung resistance in response to histamine before and after repeated injection of immune-complex. The test compounds are administered intratracheally either as solutions or suspensions in tragacanth. The $ED_{50}$ and $ED_{20}$ values for reversal of airways hyperreactivity and reduction of mean arterial blood pressure, respectively, are determined graphically from the dose response curves and represent those doses which cause a 50% reduction of airways hyperreactivity and a 20% reduction in blood pressure.

AGENTS OF THE INVENTION, e.g., especially of Examples 17, 19, 21, or 23, are potent inhibitors of airways hyperreactivity, with an $ED_{50}$ in this model of from about 0.005–1 µg/kg, an onset of action of about 2.5 minutes, and a duration of action of greater than 30 minutes following intratracheal administration. AGENTS OF THE INVENTION are moreover free of significant cardiovascular side effects at their effective doses, having $ED_{20}$ for reduction in blood pressure of from about 10–100 µg/kg, so that they have a wide therapeutic window for use in the reversal of airways hyperreactivity.

b. In the Rhesus Monkey:

A similar selectivity of action is seen in the rhesus monkey. Rhesus monkeys (male and female, body wt 6–15 kg) known to be normal responders to methacholine (MeCH), are anaesthetised (initial: ketamine 10 mg/kg i.m., maintenance: thiopental 8 mg/kg/h i.v.). A cuffed pediatric endotracheal tube (5.0 cm) is then introduced into the trachea (xylocaine: topical administration at the epiglottus) and basal lung resistance measured. Drug effects on cardiovascular parameters (heart rate, systolic, and distolic blood pressure) and respiratory rate are measured simultaneously.

Test substances are administered by inhalation of either a solution or a suspension in an appropriate vehicle (for example 30% polyethylene glycol in water or 5% ethanol in water) over a period of ten minutes during inspiration as an aerosol generated by a nebulizer. 15 minutes after drug administration, a single MeCH challenge (0.6 to 2.5 mg/ml solution, estimated to produce approximately a 50–100% change from baseline) is performed and the % inhibition calculated from first methacholine response.

AGENTS OF THE INVENTION produce potent, dose-dependent inhibition of bronchoconstriction in the above test method at concentrations of from about 0.025 mg/ml to about 50 mg/ml. The compound of example 21, for example, inhibits methacholine-induced brochoconstriction 77% at a dose of 1 mg/ml without any measurable effect on cardiovascular parameters or respiratory rate.

TEST 2: BRONCHORELAXATION

AGENTS OF THE INVENTION are tested in cryopreserved human bronchi. Small bronchi are mounted in organ baths (isometric recording under a resting tension of 1 g). the bronchi generate spontaneous tone. Concentration-response curves are determined by cumulative additions of test compound, each compound being added when the maximum effect has been produced by the previous concentration. Papaverine (300 µM) is added at the end of the concentration response curves to induce complete relaxation of the preparation, and this effect as taken as 100% relaxation.

AGENTS OF THE INVENTION show a potent bronchorelaxant effect in these human tissue preparations, with efficacy of from about 83–98% at concentrations below 1 µM.

AGENTS OF THE INVENTION are accordingly useful in particular as bronchodilator agents and as agents for the therapy of airways hyperreactivity e.g. as agents for the symptomatic as well as prophylactic treatment of obstructive or inflammatory airways disease, in particular asthma. As bronchodilator agents, AGENTS OF THE INVENTION may be employed, in particular as rescue therapy, to treat bronchoconstrictor attack, e.g. in asthma. In addition, by continued administration, AGENTS OF THE INVENTION may be used for the control, restriction or reversal of airways hyperreactivity (for example, excercise-induced asthma or natural asthma) or to provide advance protection against recurrence or bronchoconstrictor attack consequential to obstructive or inflammatory airways disease, in particular asthma. The words "treatment" and "treating" as used throughout the present specification and claims in relation to use of AGENTS OF THE INVENTION for the treatment of obstructive or inflammatory airways disease, in particular asthma, are accordingly to be understood as embracing both prophylactic as well as symptomatic (i.e. bronchodilator) modes of therapy, unless otherwise specified.

In accordance with the foregoing the present invention also provides:

4. A method for the treatment of any disease or condition herein specified; in particular 4.a A method for the treatment of obstructive or inflammatory airways disease; including 4.a.1 A method for the symptomatic treatment of inflammatory or obstructive airways disease, e.g. of effecting bronchodilation; or 4.a.2 A method for the prophylactic treatment of inflammatory or obstructive airways disease, e.g. for the treatment of airways hyperreactivity;

in a subject in need thereof, which method comprises administering to said subject an effective amount of an AGENT OF THE INVENTION:

or, in the alternative:

5. An AGENT OF THE INVENTION for use as a pharmaceutical, e.g. for use in the treatment of any disease or condition as herein specified, in particular for use in the treatment of obstructive or inflammatory airways disease, e.g. as indicated under 4.a.1 or 4.a.2 above; or 6. A pharmaceutical composition comprising an AGENT OF THE INVENTION, or use of an AGENT OF THE INVENTION in the preparation of a pharmaceutical composition, for use in the treatment of any disease or condition herein specified, in particular for use as set forth under 5 above.

Inflammatory or obstructive airways diseases to which the present invention is applicable include asthma of whatever type or genesis including both intrinsic and, especially, extrinsic asthma. They are useful for the treatment of allergic asthma, whether atopic, (i.e. IgE-mediated) or non-atopic, as well as, for example, bronchitic asthma, exercise induced asthma, occupational asthma, asthma induced following bacterial infection and other non-allergic asthmas. Treatment of asthma is also to be understood as embracing treatment of subjects, e.g. of less than 4 or 5 years of age, exhibiting wheezing symptoms, in particular at night, and diagnosed or diagnosable as "wheezy infants", an established patient category of major medical concern and now more correctly identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g. of acute asthmatic or bronchoconstrictor attack.

It may further be evidenced by reduced requirement for other, symptomatic therapy, i.e. therapy for or intended to restrict or abort symptomatic attack when it occurs, for example anti-inflammatory (e.g. corticosteroid) or bronchodilatory (e.g. $\beta_2$ adrenergic) therapy.

Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant from any previously administered symptomatic asthma therapy.

Inflammatory or obstructive airways diseases to which the present invention is applicable also include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and, in particular, byssinosis.

Further inflammatory or obstructive airways diseases and conditions to which the present invention is applicable include adult respiratory distress syndrome (ARDS), chronic obstructive pulmonary or airways disease (COPD or COAD), and bronchitis, as well as exacerbation of airways hyperreactivity consequent to other drug therapy, in particular other inhaled drug therapy, e.g. $\beta$-agonist bronchodilator therapy, including in particular usage of AGENTS OF THE INVENTION as bronchodilators for the treatment of chronic or acute airways obstruction as well as dyspnea, associated with any of the said diseases or conditions.

For use in the treatment of inflammatory or obstructive airways disease may be administered by any conventional route, in particular AGENTS OF THE INVENTION enterally, e.g. orally, for example in the form of tablets or capsules, or parenterally, e.g. in the form of injectable solutions or suspensions. Preferably however they will be administered by the pulmonary route, e.g. by inhalation from an appropriate nebulizer, inhaler or like device as known in the art.

Dosages employed in the treatment of inflammatory or obstructive airways disease will of course vary depending, e.g. on the particular condition to be treated, the particular AGENT OF THE INVENTION employed, the mode of administration and the effect desired. The established $ID_{50}$ in the test method Ia described above for the known inhaled bronchodilator drug salbutamol [albuterol; $\alpha^1$-[[(1,1-dimethyl ethyl)amino]-methyl]-4-hydroxy-1,3-benzenemethanol] is ca. 0.008 $\mu$g/kg, i.t. Appropriate dosages of the AGENTS OF THE INVENTION (e.g., of examples 17, 19, 21, or 23) for administration by inhalation, e.g. for suppression of airways hyperreactivity in the course of asthma therapy in humans, will thus be anticipated to be about the same as or somewhat higher than those conventionally required using salbutamol. In general, for pulmonary administration for larger mammals, e.g. humans, a suitable daily dosage delivered to the lungs will be of the order of from about 1 $\mu$g to about 1000 $\mu$g, in particular from about 10 $\mu$g to about 500 $\mu$g, suitably administered from an inhaler device with administration effected once or from 2 to 4× daily, in a series of from 1 to 4 puffs at each administration.

For oral administration a suitable daily dosage will generally be of the order of from about 0.1 to about 30 $\mu$g/kg. A suitable oral daily dosage for larger mammals, e.g. humans, will thus be of the order of from about 7 $\mu$g to about 2.1 mg for a 70 kg individual, administered in a single dose, in divided doses administered from 2 to 4× daily, or in sustained release form. Oral unit dosage forms for such use will thus suitably comprise from about 1.75 $\mu$g to about 2.1 mg AGENT OF THE INVENTION together with a pharmaceutically acceptable diluent or carrier therefor.

In this connection it is in particular to be noted that AGENTS OF THE INVENTION are generally active as bronchodilators or as agents for the treatment of airways hyperreactivity at dosages, in particular inhaled dosages, at which cardiovascular effects which would be undesirable in relation to such therapy, e.g. hypotensive/tachycardial effect are non-significant or within acceptable limits of tolerability in relation to the therapy practiced.

In accordance with the foregoing the present invention also provides:

7. A pharmaceutical composition comprising an AGENT OF THE INVENTION optionally together with a pharmaceutically acceptable diluent or carrier therefor, e.g., in inhalable form.

Such compositions may be manufactured in conventional manner, e.g. for pulmonary administration by compounding AGENT OF THE INVENTION in finely divided disperse particulate form, e.g. together with finely divided lactose as a carrier/diluent to form an inhalable powder. AGENTS OF THE INVENTION in a form suitable for pulmonary administration may be administered using a suitable inhaler device, e.g., a metered dose inhaler, so that the invention additionally includes 8. An inhaler device, e.g., a metered dose inhaler, containing AGENT OF THE INVENTION in inhalable form.

I claim:

1. A 2,2-di($C_{1-5}$alkyl)- or trans-2,2-di($C_{1-5}$alkyl)-3,4-dihydro-3-hydroxy-4-carboxamido-6-(N-arylsulfonamido)-2H-1-benzopyran; or an N-oxide thereof; or a physiologically-hydrolysable and -acceptable ester of such a benzopyran or N-oxide; or acid addition or quarternary ammonium salt of such a benzopyran, N-oxide or ester.

2. A compound of formula I

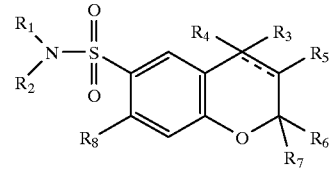

Formula I wherein $R_1$ is aryl, $R_2$ is H or $C_{1-5}$alkyl, or is $C_{2-5}$alkylene linked to $R_1$, $R_3$ is a group of formula —N($R_9$)—$COR_{10}$ wherein $R_9$ is hydrogen and $R_{10}$ is phenyl or pyridyl or $R_9$ and $R_{10}$ together are 1,3-butadienylene or represent a group of formula —(CH$_2$)$_n$— or

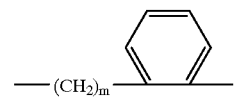

in which n is an integer of from 3 to 5 inclusive and m is 1 or 2, $R_4$ is hydrogen and $R_5$ is hydroxy in the trans position with respect to $R_3$, or $R_4$ and $R_5$ together represent an additional bond as indicated by the dotted line, $R_6$ and $R_7$ are, independently, $C_{1-5}$alkyl, and
$R_8$ is hydrogen or $C_{1-5}$alkyl;
or N-oxide thereof;
or physiologically-hydrolysable and -acceptable ester of such a compound or N-oxide, or acid addition or quarternary ammonium salt of such a compound, N-oxide or ester.

3. A compound according claim 2 selected from
a. trans-1,2,3,4-tetrahydro-1-[[3,4-dihydro-2,2-dimethyl-3-hydroxy-4-(2-oxo-piperidin-1-yl)-2H-1-benzopyran-6-yl]sulphonyl]quinoline
b. trans-N-phenyl-3,4-dihydro-2,2-dimethyl-3-hydroxy-4-(2-oxo-piperidin-1-yl)-2H-1-benzopyran-6-sulphonamide
c. trans-N-(4-methoxyphenyl)-3,4-dihydro-2,2-dimethyl-3-hydroxy-4-(2-oxo-piperidin-1-yl)-2H-1-benzopyran-6-sulphonamide
d. trans-N-methyl-N-phenyl-3,4-dihydro-2,2-dimethyl-3-hydroxy-4-(2-oxo-piperidin-1-yl)-2H-1-benzopyran-6-sulphonamide
e. trans-N-methyl-N-(4-methoxyphenyl)-3,4-dihydro-2,2-dimethyl-3-hydroxy-4-(2-oxo-piperidin-1-yl)-2H-1-benzopyran-6-sulphonamide
f. trans-N-methyl-N-(3-methoxyphenyl)-3,4-dihydro-2,2-dimethyl-3-hydroxy-4-(2-oxo-piperidin-1-yl)-2H-1-benzopyran-6-sulphonamide
g. trans-N-methyl-N-(4-fluorophenyl)-3,4-dihydro-2,2-dimethyl-3-hydroxy-4-(2-oxo-piperidin-1-yl)-2H-1-benzopyran-6-sulphonamide
h. trans-N-methyl-N-(4-trifluoromethylphenyl)-3,4-dihydro-2,2-dimethyl-3-hydroxy-4-(2-oxo-piperidin-1-yl)-2H-1-benzopyran-6-sulphonamide
i. trans-N-methyl-N-(3-trifluoromethylphenyl)-3,4-dihydro-2,2-dimethyl-3-hydroxy-4-(2-oxo-piperidin-1-yl)-2H-1-benzopyran-6-sulphonamide
j. trans-N-methyl-N-(pyridin-4-yl)-3,4-dihydro-2,2-dimethyl-3-hydroxy-4-(2-oxo-piperidin-1-yl)-2H-1-benzopyran-6-sulphonamide
k. trans-N-methyl-N-(pyridin-3-yl)-3,4-dihydro-2,2-dimethyl-3-hydroxy-4-(2-oxo-piperidin-1-yl)-2H-1-benzopyran-6-sulphonamide
l. trans-N-ethyl-N-phenyl-3,4-dihydro-2,2-dimethyl-3-hydroxy-4-(2-oxo-piperidin-1 -yl)-2H-1-benzopyran-6-sulphonamide
m. trans-[3,4-dihydro-2,2-dimethyl-3-hydroxy-6-[(1,2,3,4-tetrahydroquinolin-1-yl)sulphonyl]-2H-1-benzopyran-4-yl]-3-pyridinecarboxamide
n. trans-[3,4-dihydro-2,2-dimethyl-3-hydroxy-6-[(N-methyl-N-phenylamino)sulphonyl]-2H-1-benzopyran-4-yl]-3-pyridinecarboxamide
o. trans-[3,4-dihydro-2,2-dimethyl-6-[(N-ethyl-N-phenylamino)sulphonyl]-3-hydroxy-2H-1-benzopyran-4-yl]-3-pyridinecarboxamide
p. trans-N-methyl-N-phenyl-3,4-dihydro-4-(1,2-dihydro-2-oxo-1-pyridyl)-2,2-dimethyl-3-hydroxy-2H-1-benzopyran-6-sulphonamide
q. N-methyl-N-phenyl-4-(1,2-dihydro-2-oxo-1-pyridyl)-2,2-dimethyl-2H-1-benzopyran-6-sulphonamide
r. (3S, trans)-N-methyl-N-phenyl-3,4-dihydro-4-(1,2-dihydro-2-oxo-1-pyridyl)-2,2-dimethyl-3-hydroxy-2H-1-benzopyran-6-sulphonamide
s. (3S, trans)-[3,4-dihydro-2,2-dimethyl-3-hydroxy-6-[(N-methyl-N-phenylamino)sulphonyl]-2H-1-benzopyran-4-yl]-3-pyridinecarboxamide
t. (3S, trans)-[3,4-dihydro-2,2-dimethyl-3-hydroxy-6-[(1,2,3,4-tetrahydroquinolin-1-yl)sulphonyl]-2H-1-benzopyran-4-yl]-3-pyridinecarboxamide
u. (3S, trans)-N-phenyl-3,4-dihydro-2,2-dimethyl-3-hydroxy-4-(2-oxo-piperidin-1-yl)-2H-1-benzopyran-6-sulphonamide.

4. Pharmaceutical compositions comprising a compound according to claim 1, optionally in combination or association with a pharmaceutically acceptable diluent or carrier.

5. Compounds of formula I-1, I-2, or I-3

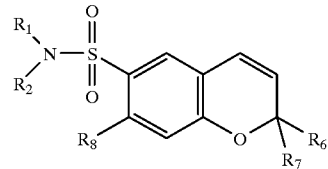

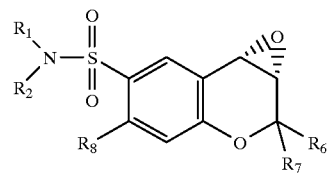

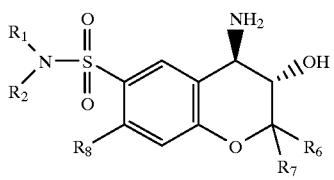

wherein $R_1$, $R_2$, $R_6$, $R_7$, and $R_8$ are as for formula I of claim 2.

6. A process for the production of a compound according to claim 1, comprising the steps of
i) for production of a benzopyran according any of claims 1 through 3, reacting a 1a,7b-dihydro-2,2-di($C_{1-5}$alkyl)-6-(N-arylsulfonamido)-2H-oxireno[c][1]benzopyran with an alkali metal salt of a carboxamide, and optionally dehydrogenating the product thus obtained; or acylating and, when required, alkylating the amino group of a 2,2-di($C_{1-5}$alkyl)- or trans-2,2-di($C_{1-5}$alkyl)-3,4-dihydro-3-hydroxy-4-amino-6-(N-arylsulfonamido)2H-1-benzopyran; or
ii) for the production of a benzopyran N-oxide or physiologically-hydrolysable and -acceptable ester of a benzopyran or benzopyran N-oxide according to claim 1, esterifying a benzopyran or benzopyran N-oxide according to claim 1 having a free hydroxy group or moiety to introduce an appropriate ester grouping and/or oxidising a benzopyran or physiologically-hydrolysable and -acceptable ester thereof according claim 1;
and recovering the obtained benzopyran, benzopyran N-oxide or physiologically-hydrolysable and-acceptable ester thereof in free or in acid addition or quarternary ammonium salt form.

7. A compound according to claim 2 wherein $R_1$ is phenyl, fluorophenyl, trifluoromethyllphenyl, methoxyphenyl, or pyridyl; $R_2$ is methyl, ethyl, or hydrogen; or $R_1$ and $R_2$ together with N form a 1,2,3,4-tetrahydroquinolin-1-yl group.

8. A compound according to claim 2 wherein $R_{10}$ is pyridyl or $R_9$ and $R_{10}$ together are 1,3-butadienylene, trimethylene or tetramethylene.

9. A compound according to claim 8 wherein $R_{10}$ is 3-pyridyl.

10. A compound according to claim 8 wherein $R_9$ and $R_{10}$ together are tetramethylene.

11. A compound according to claim 2 wherein $R_4$ is hydrogen and $R_5$ is hydroxy.

12. A compound according to claim 2 of formula Ia

Formula Ia

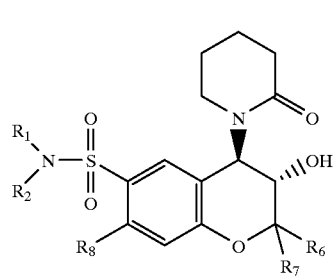

13. A compound according to claim 2 of formula Ib

Formula Ib

14. A compound according to claim 2 of formula Ic

Formula Ic

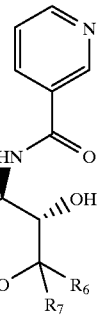

15. A method of treating or preventing obstructive or inflammatory airways disease comprising administering a compound according to claim 1 to a patient in need of such treatment or prevention.

16. A method of treating or preventing obstructive or inflammatory airways disease comprising administering a compound according to claim 2 to a patient in need of such treatment or prevention.

17. A method of treating or preventing obstructive or inflammatory airways disease comprising administering a compound according to claim 3 to a patient in need of such treatment or prevention.

18. A pharmaceutical composition comprising a compound according to claim 2, optionally in combination or association with a pharmaceutically acceptable diluent or carrier.

19. A pharmaceutical composition comprising a compound according to claim 3, optionally in combination or association with a pharmaceutically acceptable diluent or carrier.

\* \* \* \* \*

UNITED STATES PATENT AND TRADEMARK OFFICE
CERTIFICATE OF CORRECTION

PATENT NO. : 5,905,156
DATED : May 18, 1999
INVENTOR(S) : PAUL W. MANLEY

It is certified that error appears in the above-indentified patent and that said Letters Patent is hereby corrected as shown below:

Column 16, Example 23, line 55, delete "N-phenyl-"

Signed and Sealed this

Thirtieth Day of November, 1999

Attest:

Q. TODD DICKINSON

Attesting Officer

Acting Commissioner of Patents and Trademarks